United States Patent [19]

Woo et al.

[11] Patent Number: 5,130,116
[45] Date of Patent: Jul. 14, 1992

[54] RADIOTHERAPEUTIC IMMUNOCONJUGATES LABELED WITH IODINE-125

[75] Inventors: David V. Woo, Downingtown; Zenon Steplewski, Malvern; Jeffrey A. Mattis, West Chester, all of Pa.

[73] Assignee: Centocor, Inc., Malvern, Pa.

[21] Appl. No.: 530,091

[22] Filed: May 29, 1990

Related U.S. Application Data

[63] Continuation-in-part of Ser. No. 256,655, Oct. 12, 1988, abandoned.

[51] Int. Cl.$^5$ ............... A61K 39/395; A61K 43/00
[52] U.S. Cl. ............... 424/1.1; 424/85.91; 530/402
[58] Field of Search ............... 424/1.1, 85.91; 530/402

[56] References Cited

U.S. PATENT DOCUMENTS 3,927,193 12/1975 Hansen et al.
4,331,647 5/1982 Goldenberg.
4,430,318 2/1984 Langone.

OTHER PUBLICATIONS

Sugiyama et al., *Cancer Res.* 48: 2768–2773 (1988).
T. Lindmo et al., *Cancer Research*, 45:5080–5087 (1985).
E. Boven et al., *Blood*, 67(2):429–435 (1986).
M. K. Markwell and C. F. Fox, *Biochemistry*, 17(22):4807–4817 (1978).
A. H. Ross et al., *Biochemical and Biophysical Research Communications*, 135(1):297–303 (1986).
K. Koprowski et al., *Somatic Cell Genetics*, 5(6):957–972 (1979).
H. F. Sears et al., *Journal of Surgical Research*, 31(2):145–150 (1981).
Goldenberg et al., *In: Immunodiagnosis Of Cancer*, Part 1, (R. B. Herberman and K. R. McIntire, eds), pp. 265–304, Marcel Dekker, Inc. New York, (1979).
Barth et al., *Hybridoma*, :543–550 (1986).
D. R. Shaw et al., *J. Immunol.*, 138:4534–4538 (1987).
G. Mariani et al., *J. Nucl. Med. Biol.*, 16(2):147–150 (1989).

*Primary Examiner*—John S. Maples
*Attorney, Agent, or Firm*—Hamilton, Brook, Smith & Reynolds

[57] ABSTRACT

A radiotherapeutic immunoconjugate comprising a tumor specific monoclonal antibody, or fragment thereof, and an Auger electron emitting radionuclide, wherein the tumor specific monoclonal antibody or fragment is capable of tumor nucleus localization of the radionuclide and method of using it is disclosed. The radiotherapeutic immunoconjugate is administered in a therapeutically effective amount to patients having or suspected of having a malignancy reactive with the antibody or fragment.

4 Claims, 7 Drawing Sheets

RADIOTHERAPEUTIC IMMUNOCONJUGATES LABELED WITH IODINE-125

RELATED APPLICATION

The present application is a continuation-in-part of co-pending application Ser. No. 07/256,655, filed Oct. 12, 1988, now abandoned by David V. Woo, Zeon Steplewski and Jeffrey A. Mattis.

BACKGROUND OF THE INVENTION

Immunotherapeutic techniques designed to localize radioisotopes proximate to cancer cells are being widely tested with a variety of radionuclides. In theory, such radionuclides could deliver sufficient radiation to destroy a tumor through numerous cell layers distant from the primary decay event. However, clinical studies indicate that radiolabelled monoclonal antibodies are capable of localizing less than about 0.004% of an injected dose of 1 gram of radioactivity in a human tumor. As a result it is uncertain whether monoclonal antibodies will be capable of delivering therapeutic quantities of standard radiation to a tumor volume without causing significant radiation toxicity to the remaining body.

Therapeutic applications of immunoconjugates of radioactive iodine in patients has been limited to use of iodine-131 ($^{131}$I). Recently, studies relating to the in vitro cytotoxicity of radioactive iodine-125 ($^{125}$I) labelled monoclonal antibodies have been reported in the technical literature. For example, T. Lindmo et al. in *Cancer Research* 45:5080 (1985) discloses specific killing of human melanoma cells by a $^{125}$I labelled murine monoclonal antibody directed against a M$_r$ 250,000 melanoma-associated antigen. E. Boven et al. in *Blood* 67:429 (1986) discloses selective-cytotoxicity of $^{125}$I-labelled murine monoclonal antibody specific for the T65 antigen on human malignant T cell lines. Boven et al. reference disclose that prolonged exposure times were necessary only under frozen conditions to achieve a low degree of cell killing. It is believed that the cell killing is due to radiation damage within the cell caused by the Auger electrons of $^{125}$I. Clinically useful applications for $^{125}$I-labelled monoclonal antibodies are of significant interest to those in the biomedical field.

SUMMARY OF THE INVENTION

The present invention provides a method for treating a tumor or malignancy using a radiotherapeutic immunoconjugate comprising a tumor specific monoclonal antibody, or fragment thereof, and an Auger electron emitting radionuclide, wherein the tumor specific monoclonal antibody or fragment is capable of tumor cell nucleus localization of the radionuclide. The radiotherapeutic immunoconjugate is administered in a therapeutically effective amount to patients having or suspected of having a malignancy reactive with the antibody or fragment.

In one embodiment, the invention provides a radiotherapeutic immunoconjugate comprising a murine monoclonal antibody, or fragment thereof, specific for the 17-1A antigen (CA17-1A) and $^{125}$I. The invention further provides a method for treating 17-1A positive malignacies comprising administering a therapeutically effective amount of the above radiotherapeutic immunoconjugate.

The present method allows a tumor-lethal dose radiation to be effectively localized at the tumor cell nucleus, thereby maximizing the effect of the radiation at the tumor site while minimizing radiation damage to healthy tissue.

DETAILED DESCRIPTION OF THE INVENTION

Figure 1A:
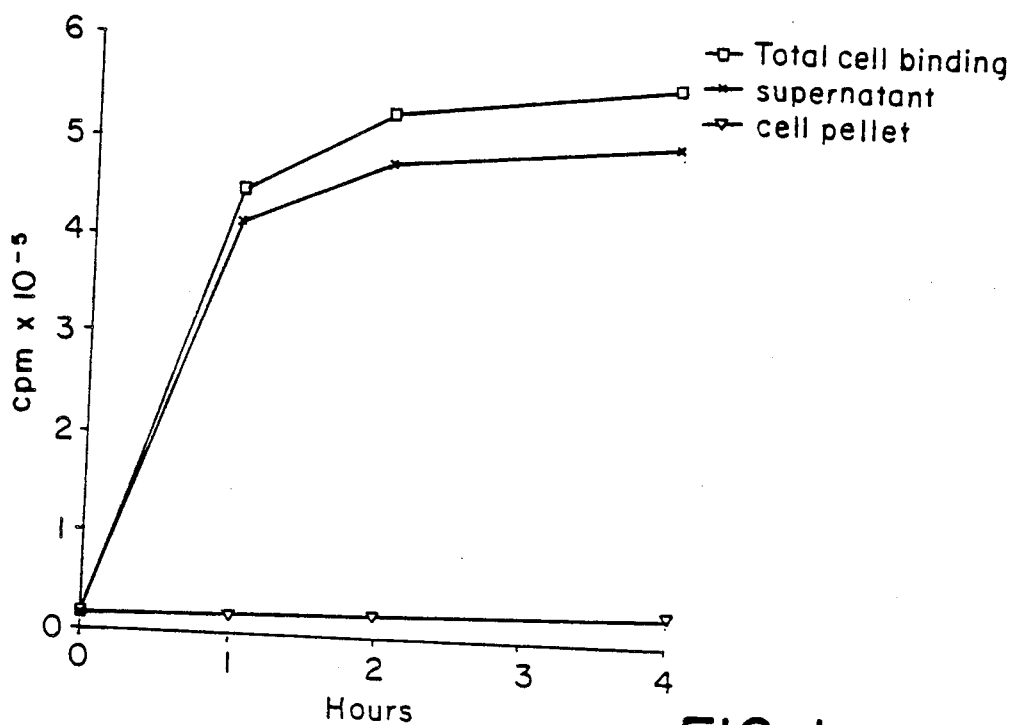
FIG. 1a is a graph showing internalization of $^{125}$I MAb 17-1A immunoconjugate in 17-1-A-positive tumor cells (SW1116) following incubation at 0° C.

This invention relates to a cancer therapy method which employs an immunoconjugate comprising a tumor-specified monoclonal antibody, or fragment thereof, and an Auger electron-emitting radionuclide, wherein the tumor-specific monoclonal antibody or fragment is capable of tumor cell nucleus localization. As used herein, the expression "tumor cell nucleus localization" means that the antibody or fragment demonstrates specific incorporation into the nucleus of mammalian cells and its related components (e.g., nuclear membrane, nucleoplasm, chromatin, chromosomes, nucleolus, nucleosomes, DNA and RNA). It has been found that the present immunoconjugates are capable of selective cytotoxity for tumor tissue without harming normal tissues.

Tumor specific monoclonal antibodies useful in the invention can be obtained by immunizing an animal with a biological sample containing tumor-associated antigen, forming a fused cell hybrid between antibody producing cells from the animal and myeloma cells, cloning the resulting hybrid and selecting clones which produce antibodies that bind to the tumor associated antigen. Techniques for immunizing animals, forming fused cell hybrids, and selecting clones with the desired binding specificity are known in the art. The preparation of antibody fragments from intact antibodies are also well known to those skilled in the field of immunology. In a preferred embodiment of the present invention, a biological sample containing the 17-1A antigen (CA17-1A) is employed to immunize an animal, and a monoclonal antibody, or fragment thereof, having specificity to CA17-1A is employed in the invention.

The monoclonal antibody 17-1A (herein after referred to as MAb 17-1A) has been reported to bind to a tumor-specific antigen (hereinafter "CA17-1A") associated with gastrointestinal adenocarcinomas. Koprowski, H., Steplewski, Z., Mitchell, K., Herlyn, M., Herlyn, D. & Fuhrer, J. P. *Somat. Cell Genet.*, 5:957-972 (1979); Sears, H. F., Herlyn, D., Herlyn, M., Grotzinger, P. J., Steplewski, Z., Gerhard, W. & Koprowski, H. J. *Surg. Res.*, 31:145-150 (1981)). The antigen has been characterized, and is described as a cell surface protein with two subunits of 30,000 to 40,000 daltons. Ross, A. H., Herlyn, D., Iliopoulos, D., and Koprowski, H. *Biochemical and Biophys Res Comm.*, 135:297-303 (1986).

Auger electron-emitting radionuclides are known in the art. For example, radioactive iodine-125 ($^{125}$I) decays be electron capture ($T_{\frac{1}{2}}$60.5 days) to the metastable state of tellurium-125 m which undergoes immediate decay events by internal conversion (93%) and by gamma ray emission (7%) to the tellurium-125 daughter. Due to inner shell vacancies produced during decay, a complex series of electron shell rearrangements occur resulting in low energy x-rays (27-35 keV) and a cascade of low energy electrons. This form of radiation is particularly lethal when delivered in close proximity to the cell nucleus, inducing chromosome breaks and other damage to the nuclear material which severely impairs the ability of the tumor cells to grow.

Tumor specific monoclonal antibodies, or fragments thereof, are labelled with an Auger electron emitting radionuclide by any of the many known labelling methods. The preferred technique for $^{125}$I labeling is that of Markwell, M. A. K. & Fox, C. F. *Biochemistry* 17:4807-4817 (1978), the teaching of which are incorporated herein by reference. Antibodies can also be labeled with radioiodine by a variety of other well known procedures (e.g., Chloramine T, Bolton-Hunter, Lactoperoxidase, etc).

In the method of the invention, the radiotherapeutic immunoconjugate is administered in a therapeutically effective amount to a patient having or suspected of having a tumor or malignancy reactive with the antibody of fragment component of the immunoconjugate. Methods for administering radiotherapeutic immunoconjugates to patients are known in the art. Preferably, the present immunoconjugate is administered in an amount sufficient to delivery a dosage of from about 20 to 200 milliCuries of radioactivity representing mass quantities of antibody of about 20 to 200 mg.

Although not wishing to be bound by theory, it is necessary that in order for the present $^{125}$I labeled monoclonal antibody to be effective, the monoclonal antibody must first be internalized significantly into the cell as a result of binding to its specific membrane antigen. It is believed that for maximum cell killing efficiency of a 17-1A positive tumor, the $^{125}$I radiolabeled monoclonal antibody or its radioactive breakdown products, must bind directly to the nucleus.

The method of the present invention provides an effective method for localizing radiation to tumor cells. The method results in the radiolabeled tumor specific antibody specifically targeting the tumor cell, and the evidence provided in the Examples below indicates that the antibody is internalized into the tumor cell, and the radionuclide is thereby placed in close proximity to the tumor cell nucleus. The radiation emitted by the Auger-electron emitter particularly lethal at this close range to the tumor cell, but not to surrounding tissue, due to its subcellular range. The radiation damage to the cells is ultimately due to chromosomal damage, which results in irreparable damage to, and provides efficient killing of the tumor cells.

The invention is further described by the following examples wherein all parts and percentages are by weight and degrees are Celsius.

EXAMPLES

Materials and Methods

Tumor cell lines and monoclonal antibodies

Human colon cancer SW1116 cells were cultured in RPMI 1640 medium supplemental with 20% fetal calf serum. Another cell population designated WISH, human amnion cells, obtained from the American Type Culture Collection (Rockville, MD) was cultured in the same medium containing 10% fetal calf serum. This cell line contained no tumor specific antigens that binds the MAb 17-1A. The cell lines were maintained in a humidified incubator with an atmosphere of 5% $CO_2$ in air at 37° C. For the following examples and control experiments, all cells in log phase were harvested by removing the medium, washing with 0.05% trypsin containing 0.02% EDTA and 5 $\mu$g/ml DNAase and resuspended in fresh medium to various cell concentrations depending upon the study.

The monoclonal antibodies 17-1A, IgG(2a) isotype; chimeric 17-1A (c17-1A); 1116-NS-19-9, IgG(2a) isotype; and R11D10, IgG(2a) isotype were employed in the assays. The 1116-NS-19-9 monoclonal antibody binds to a colon cancer antigen that is shed from the SW1116 cell line. The R11D10 monoclonal antibody demonstrates reactivity with cardiac myosin and was used as an nonimmunoreactive control antibody.

Radioiodination

All monoclonal antibodies were labeled with $^{125}$I using the Iodogne TM (Pierce Chemical Co.) method. Markwell, M. A. K. & Fox, C. F. *Biochemistry* 17:4807-4817 (1978). To Iodogen TM coated tubes, 200 $\mu$g of antibody (10 mg/mL, Albumin free) were added followed by 80 $\mu$L of PBS (0.1 M phosphate buffer in saline, pH 7.0). Approximately 2.5 milliCuries of Na$^{125}$I (carrier free, Dupont NEN, Boston, MA) were immediately added and the resulting reaction was carried out for 10 minutes. The reaction was quenched using an ascorbic acid solution (0.5 mL, 10 mg/mL) and the bound $^{125}$I separated from any free iodide ion on a Sephadex G-25M column (Pharmacia Co., Uppsala Sweden) which was prewashed with a 2% Human serum albumin saline solution. The radiolabeled antibody was eluted in the void volume and assayed in a sodium iodide gamma scintillation counter.

Immunoreactivity and Internalization

Immunoreactivity of the $^{125}$I labeled MAb 17-1A was evaluated by indirect cell binding with various concentrations of radioactive antibody. SW1116 cells ($5 \times 10^5$) were incubated in 100 $\mu$l of RPMI 1640 medium (20% fetal calf serum) at 37° C. for 4 hours in microfuge tubes (Beckman) with various concentrations of labeled antibody (0.039-20 $\mu$Ci/mL). After incubation, the cells were centrifuged and washed twice with PBS (pH7.4) containing 10% horse serum (Flow Laboratories, VA) and 0.02% NaN$_3$. The final cell pellet was counted in a sodium iodide gamma scintillation counter set to detect the 35 keV x-rays of $^{125}I$.

The internalization of $^{125}I$ labeled MAb 17-1A was determined by incubating $2 \times 10^6$ cells in RPMI 1640 medium (20% fetal calf serum) in a fixed concentration of antibody (0.5 μCi/mL, 0.72 ug, 10 μL) for various time periods (from 0 to 48 hours). After incubation at 37° C. with occacional shaking, the mixture was centrifuged and washed four times with 1 mL of the PBS containing 10% horse serum and 0.02% $NaN_3$. After the final centrifugation, the supernatants were discarded and the cell pellet assayed for radioactivity. The total cell binding (cell-associated) radioactivity was determined. The cell pellets were then resuspended in 0.2 mL of glycine-HCl buffer, pH 2.8, and incubated for 20 minutes at 0° C. The total cell-associated radioactivity was separated by centrifugation into the cell pellets which contained the acid-unremovable portion and the supernatants which contained the acid-removable portion of the radioactivities. The supernatants and the cell pellets were separately assayed for their radioactive content. This procedure was then repeated with the incubation periods done at 0° C.

Assays for Chromosomal Damage

Approximately 10 cells in log phase were innoculated into a flask (25 cm²) containing 5 mL of growth medium. After incubation at 37° C. for 24 hours, various concentrations of $^{125}I$ labeled monoclonal antibodies or control agents were added to the culture and the resulting mixtures were further incubated for 48 hours. The cells were arrested in metaphase with demecolcine (0.06 μg/mL) 5 hours prior to termination of the incubation. The monolayers were dispersed by incubation with 0.05% trypsin for 10 minutes and the cells treated with 10 mL of 0.075 M KCl as a hypotonic for 40 minutes at 37° C. The resulting cell suspension was transferred to 15 mL centrifuge tubes and gently mixed with 5 mL of freshly prepared Carnoy's solution (acetic acid:methanol, 1:3) and incubated at ambient temperature for 10 minutes. The cells were harvested by centrifuging at 1000 rpm for 10 minutes, removing the supernatant, and gently resuspending in 10 mL of fresh Carnoy's solution. The incubation period at ambient temperature, centrifugation, and resuspension were repeated three times. Finally 3-4 drops of cell suspension were dropped onto clean, cold wet slides and allowed to air dry. The slides were then stained with Giemsa. A total of 100 cells from duplicate experiments (50 cells from each) were analyzed at each dose level under oil immersion. They were scored for chromatid breaks, acentric fragments, multicentric chromosomes, rings, and chromatid exchanges.

In the quantitative analysis, the various types of chromosomal abberations were expressed as chromosome breaks (CB). Fragment and chromatid breaks were assigned one break; dicentric and ring figures were scored as two breaks. In instances of chromatid exchange, the number of breaks were determined by the configuration and number of chromosomes involved in the exchange figure.

For determination of micronuclei (MN), procedures for cell culture and the $^{125}I$ antibody treatments were the same as the chromosome assay. After trypsinization and swelling in hypotonic KCl for 10 minutes at 37° C., the single-cell suspensions were fixed in ice-cold Carnoy's fixative, and were dropped onto clean glass slides. Cytoplasmic structures were scored as MN if they showed the same Giemsa staining reaction as the nucleus, were clearly resolved from the nucleus (to distinguish them from nuclear blebs), and had diameters that were 1/6 to ⅓ of the nucleus. A total of 2000 cells from duplicate experiments (1000 from each) were scored and averaged for each data point.

Cell Survival

Exponentially growing cells were trypsinized and serial dilutions of cell suspensions were prepared. An appropriate number of viable single cells ($1 \times 10^3 - 4 \times 10^4$), depending upon the expected plating efficiency and surviving fraction, were seeded onto 3-5, 60 mm petri dishes containing 4 mL of growth medium. The different concentrations of $^{125}I$ labeled MAb 17-1A (0-40 μCi/mL) and control agents were added at the same time. The cells were incubated at 37° C. for 48 hours. The doubling time for the SW1116 cells were determined to be about 48 hours (direct cell counting by typan blue exclusion of known cell numbers at various time intervals). After exposure for 48 hours with the test agents, the medium was aspirated and cells washed once with PBS. New growth medium was added and the cells incubated for another 19 days in the humidified 5% $CO_2$ atmosphere at 37° C. to allow for colony formation. Plates were then stained with Crystal Violet (Fisher Scientific Co.) and individual colonies containing more than 50 cells wre counted. The cell survival value was determined using the following formula.

$$\text{fraction survival} = \frac{\text{mean plate count of tests}}{\text{number of cells plated} \times P.E.}$$

$$P.E. \text{ (plating efficiency)} = \frac{\text{mean plate count of controls}}{\text{number of cells plated}}$$

Duplicate independent experiments were used to determine the average fractional survival. A 17-1A-negative tumor cell line (WISH) was also used for cell survival with the radiolabeled MAb 17-1A.

RESULTS

The radiolabeling of MAb 17-1A with $^{125}I$ resulted in a specific activity of 10-12 mCi/mg. The average radioiodination yields were 90-95% efficient. This procedure can be scaled up to radiolabel much larger quantities of I-125, greater than 25 milliCuries. The immunoreactivity of the final labeled product was evaluated in a simple cell binding assay (FIG. 1) which indicates the relative amount of radioactivity bound to tumor cells (SW1116) exposed to various concentrations of $^{125}I$ labeled antibody compared to an nonimmunoreactive $^{125}I$ antibody (R11D10) which showed negligible binding (not graphed due to being off scale). The amount of radioactivity bound by cells exposed to MAb 17-1A becomes a constant fraction when the radioactive concentration is greater than 10 μCi/mL. For the number of cells ($2 \times 10^5$) used in this assay, 0.67 pCi of $^{125}I$ appear maximally bound per cell or 1.5 dpm/cell. This amount to approximately $1.9 \times 10^5$ radioiodine atoms per cell or 0.047 picograms of antibody (assuming 1 iodine atom per antibody molecule). The radiolabeled nonimmunoreactive MAb R11D10 showed little total cell binding to the SW1116 cells. (about $2.5 \times 10-4$ dpm per cell).

The internalization of $^{125}I$ labeled MAb 17-1A by SW1116 cells was determined by measuring the cell binding at either 0° or 37° C., and using a mild acid wash to dissociate the antigen-antibody complex which released free antibody from membrane bound antigen back into solution. In these examples and experiments, the following formula was employed:

$$\% \text{ internalization} = \frac{\text{radioactive counts in cell pellet (acid-unremovable)} \times 100\%}{\text{total cell binding counts}}$$

Figure 1B:
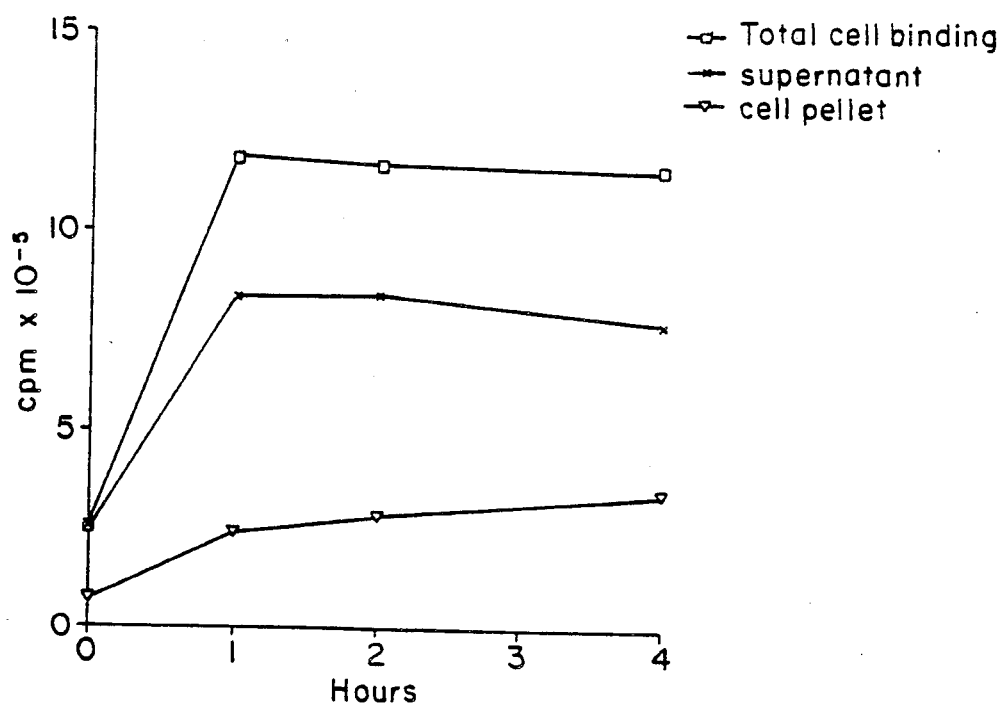
FIG. 1b shows internalization of the same immunoconjugate following incubation at 37° C.

The amount of internalized I-125 radioactivity after cells were exposed to $^{125}$I labeled MAb 17-1A was determined and the results are shown in FIG. 1a and 1b. As shown in FIG. 1a, the total cell binding curve (cell-associated radioactivity) and the supernatant curve (acid-removable radioactivity) are similar at 0° C. since greater than 90% of the antibody was dissociated from membrane bound antigen and recovered in the supernatant at the various time periods. Incubation of SW1116 cells at 37° C. (FIG. 1b) with the radioactive MAb 17-1A resulted in a significant portion of radioactivity remaining with the cell pellet (acid-unremovable) which increased with time of incubation leaving less radioactivity in the supernatant (acid-removable).

Figure 2:
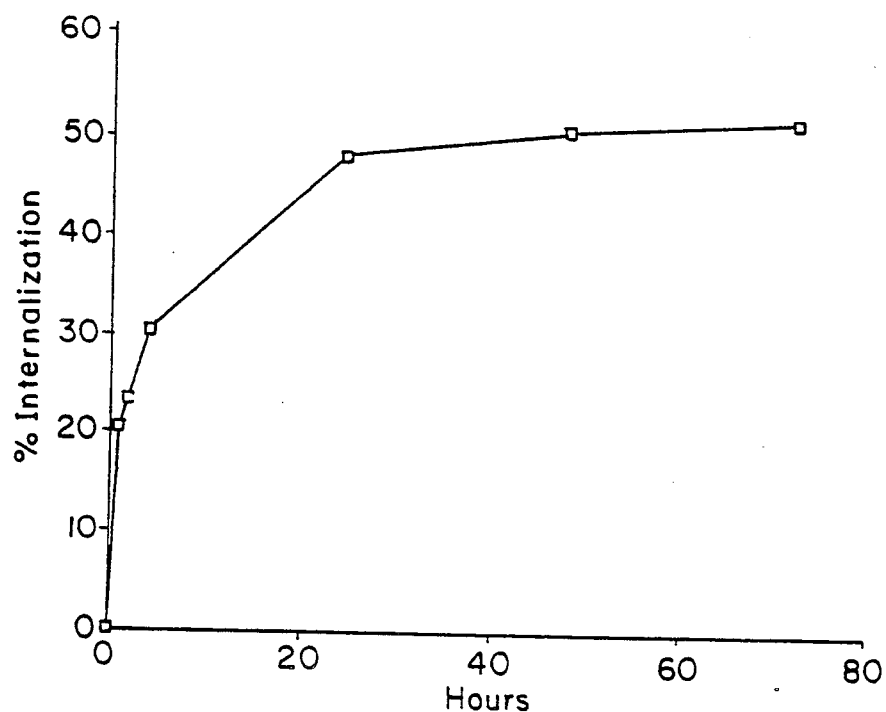
FIG. 2 is a graph showing internalization of $^{125}$I MAb 17-1A in SW1116 cells following incubation at 37° C.
Figure 3:
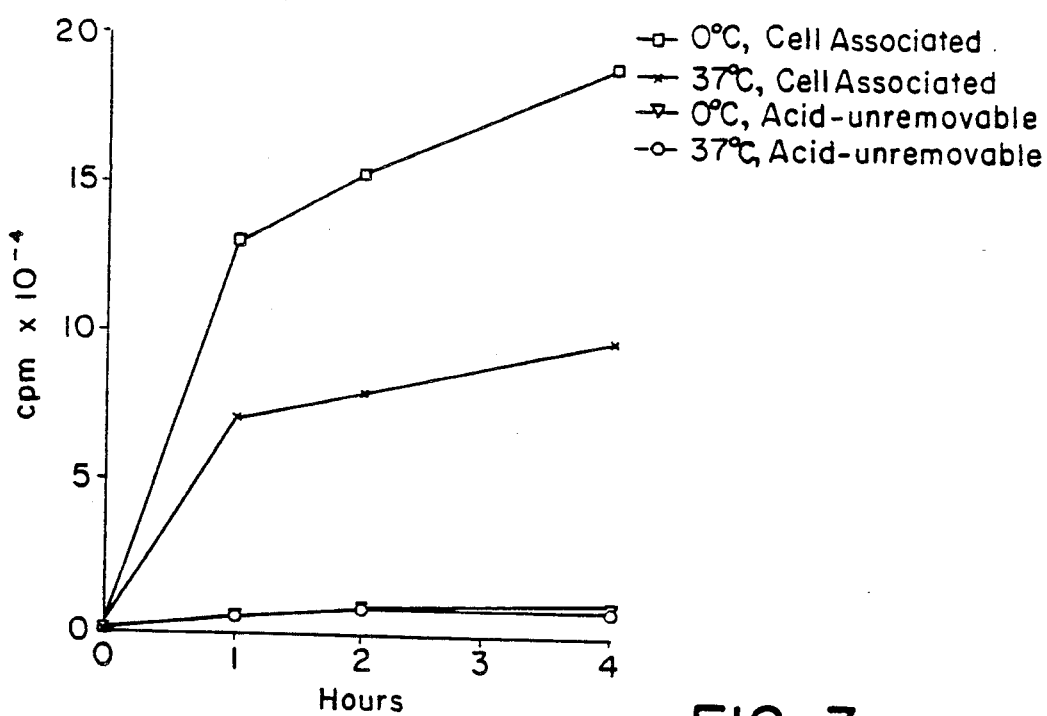
FIG. 3 is a graph showing the results of a control experiment wherein internalization of $^{125}$I MAb 1116-NS-19-9 was measured in SW1116 cells following incubation at 0° C. and 37° C.

The relative percentage internalized into the SW1116 cell increased significantly from 4 hours (29%) to 48 hours (49%) incubation as shown in FIG. 2. Therefore, the results suggest that internalization of the radioiodinated MAb 17-1A occurs after binding to its cell specific antigen and that amount internalized increases over time. Results obtained from studies with the radiolabeled ($^{125}$I) nonimmunoreactive R11D10 antibody (458–695 cpm, 0–4 hours at 37°; 372–491 cpm, 0–4 hours at 37°) and $^{125}$I labeled 1116-NS-19-9 antibody are shown in FIG. 3 and suggested that little or no internalization took place at 37° C.

Figure 4A:
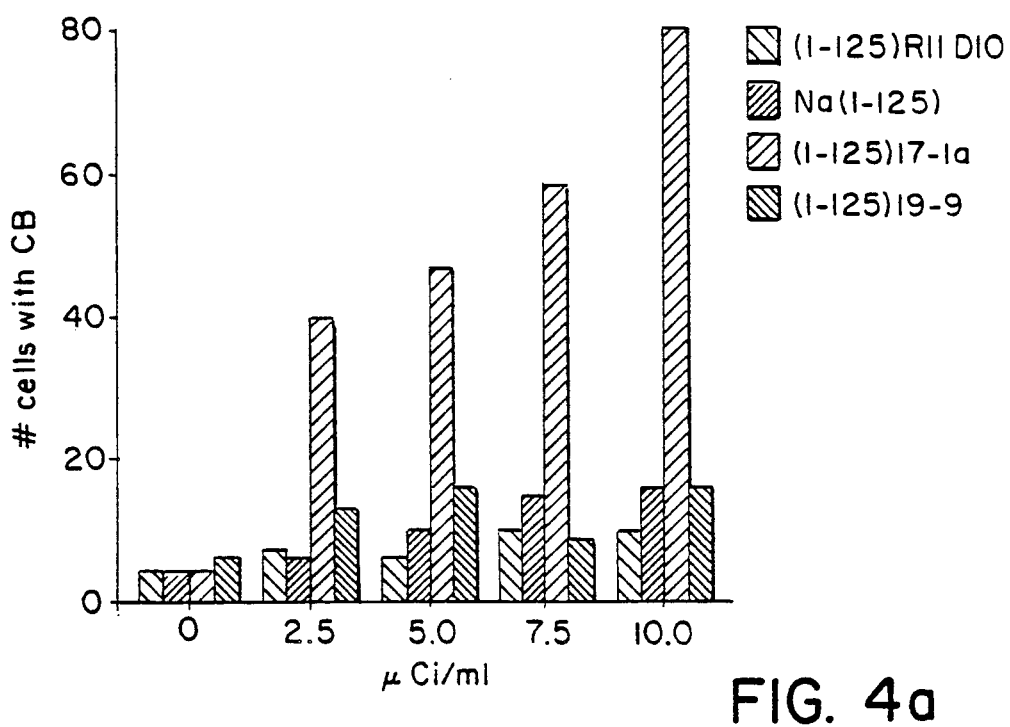
FIGS. 4a, 4b, 4c, and 4d are graphs showing the number of chromosomal aberations scored in SW1116 cells due to specified $^{125}$I labelled monoclonal antibodies and control agents.
Figure 4B:
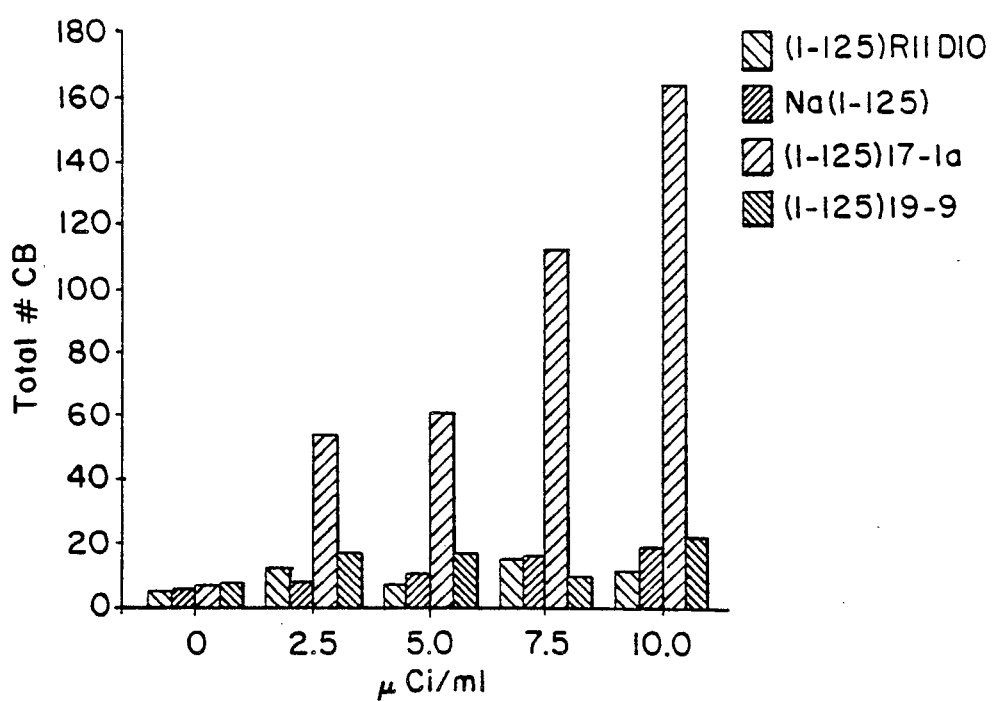
Figure 4C:
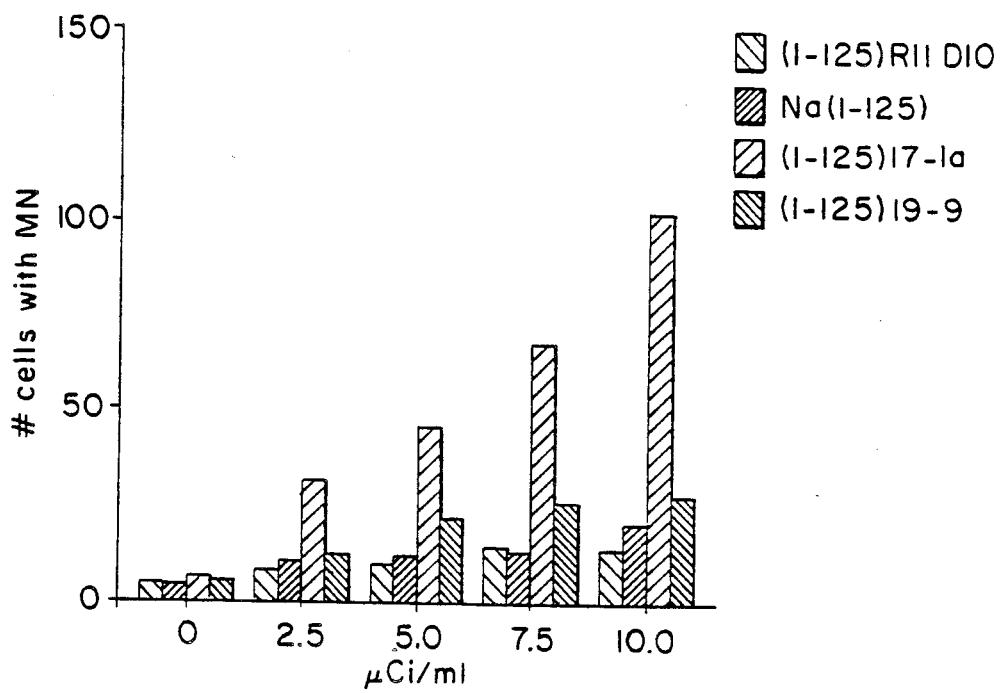
Figure 4D:
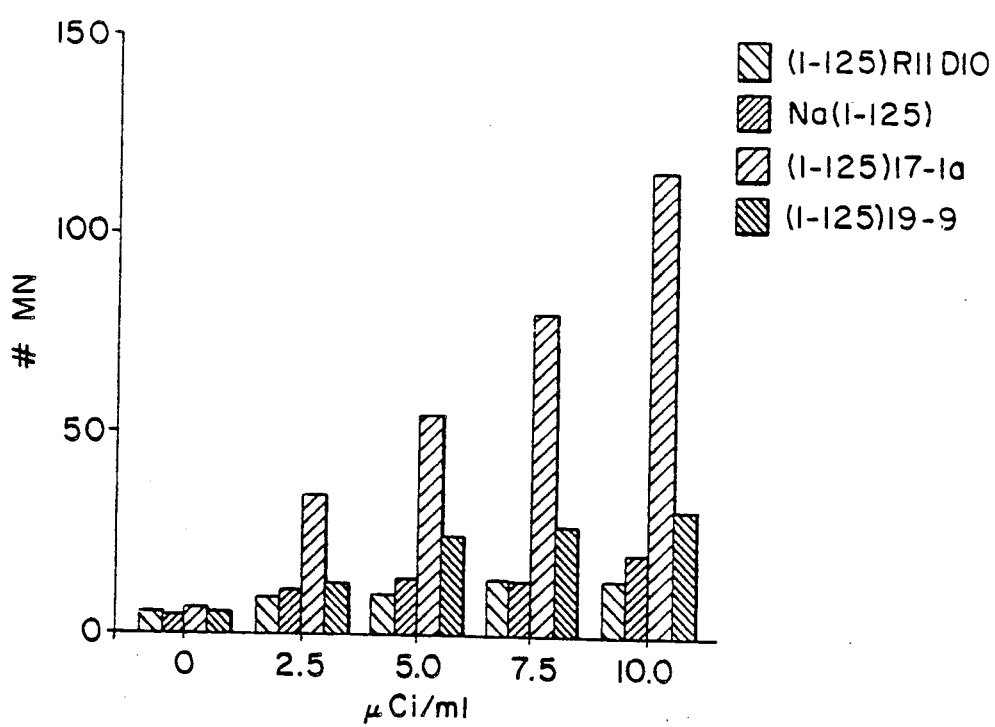

Chromosomal aberations in mitotic figures of cells exposed to increasing concentrations of radiolabeled $^{125}$I monoclonal antibodies and control agents were scored and the results are shown in FIGS. 4a, 4b, 4c, and 4d. In these experiments, the number of cells per 100 metaphases with chromosomes breaks (CB) were scored from duplicate samples which varied ±10% and the results are shown in FIG. 4a (zero μC/ml concentrations represents background chromosomal abberations which were determined at the time with each test agent). In each sample, 50 cell metaphases were analyzed. The total number of CB in 100 metaphases are shown in FIG. 4b. The results demonstrated that multiple breaks occur at higher radioactive concentrations. The number of cells with micronuclei (MN) formed per 1000 cells were also scored, and the results (average of duplicate samples which varied ±10%) are shown in FIG. 4c. The average total number of MN per 1000 cells from duplicate samples (+10% variations) are shown in FIG. 4d.

FIGS. 4a–d indicate specific nuclear damage by the $^{125}$I decay events. The $^{125}$I-R11D10 and Na$^{125}$I at increasing radioactive concentrations did not result in any increased frequency of aberations or total number of aberations. The noninternalized $^{125}$I labeled 115-NS-19-9 which binds a shed antigen on the SW1116 cells resulted in slightly greater frequency of chromosome aberations than normal control values. The Auger electron damage caused by the $^{125}$I labeled MAb 17-1A demonstrated a dose-dependent response related increase in chromosomal aberations as seen with increased frequency and total number of aberations scored (FIGS. 4a and 4b).

Figure 5:
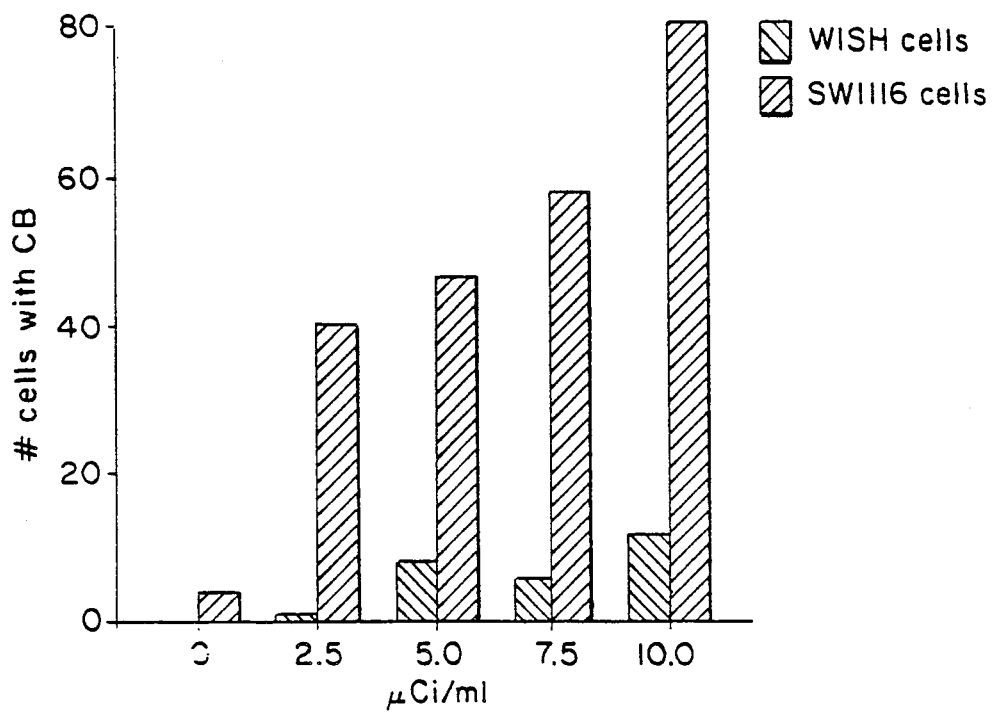
FIG. 5 is a graph showing the number of cells with chromosome breaks in SW1116 and 17-1A negative tumor cells (WISH) following incubation with $^{125}$I radiolabelled MAb 17-1A.

Chromosomal studies with a equivalent mass amounts of radioactive and nonradioactive MAb 17-1A at constant specific activity were performed in order to determine whether the cellular damage was due to $^{125}$I alone. In this experiment, numerical values were scored from duplicate samples (50 cell metaphases) with ±10% variations. FIG. 5a shows chromosomal breakds in SW1116 versus WISH cell lines exposed to $^{125}$I labeled MAb 17-1A. FIG. 5b shows the results when radiolabeled MAb 17-1A is compared to equivalent molar concentration of unlabeled MAb 17-1A in SW1116 cells and indicates no increased chromosomal damage above normal background levels for unlabeled antibody.

Chromosomal damage was not observed to any significant degree in the WISH cell line exposed to $^{125}$I labeled MAb 17-1A, as shown in FIG. 5a. Another indication of specific nuclear damage caused by radiation effect is the formation of micronuclei in cells. The mean frequency and total mean number of micronuclei per 1000 cells (mean value of 2 separate experiments) was significantly increased above control agents as shown in FIGS. 4c and 4d. These results suggest that the $^{125}$I labeled MAb 17-1A can induce specific chromosomal damage, presumably due to the Auger electrons, that increases proportionally with increasing radioactive concentration. At the higher radioactive concentrations (greater than 10 μCi/ml), there is a greater number of overall chromosome breaks (CB) due to increased multiple breaks per cell as well as an increased number of micronuclei (MN). In addition, there was about a ten-fold increase in the numbers of cells showing characteristic radiation induced pulverization of the chromosomes at the higher radioactive concentrations. The results suggest that specific chromosomal damage can be caused by an Auger electron emitter attached to a monoclonal antibody which is internalized and interacts directly with the DNA.

Figure 6:
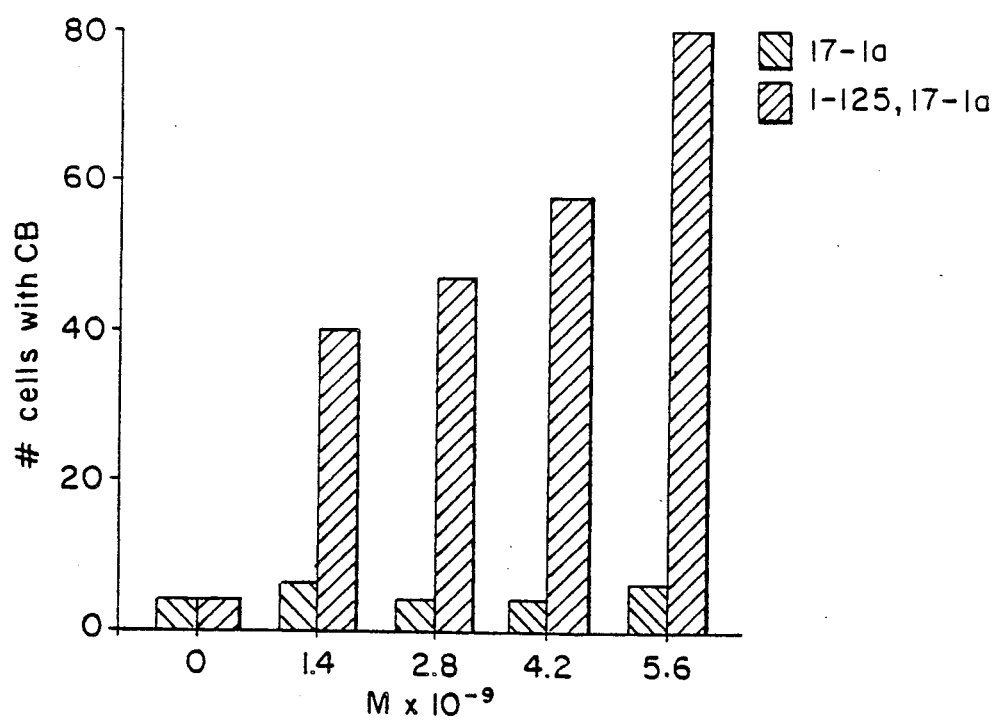
FIG. 6 is a graph showing the number of cells with chromosome breaks (CB) per 100 metaphases after exposure to various concentrations of $^{125}$I radiolabeled and unlabeled MAb 17-1A.

The effect of $^{125}$I labeled MAb 17-1A on cell survival was determined using SW1116 and WISH cell lines and the results are shown in FIG. 6. In these experiments, log (% fractional survival) was measured against radioactive concentration. Numerical results were based on the average of duplicate experiments. $^{125}$I labeled R11D10 as nonimmunoreactive antibody was compared to $^{125}$I labeled MAb 17-1A in SW1116 cells. In addition, $^{125}$I labeled MAb 17-1A cell survival in WISH cells was compared to unlabeled MAb 17-1A at equivalent molar concentrations (1.4–5.6×10$^{-9}$ M).

Figure 7:
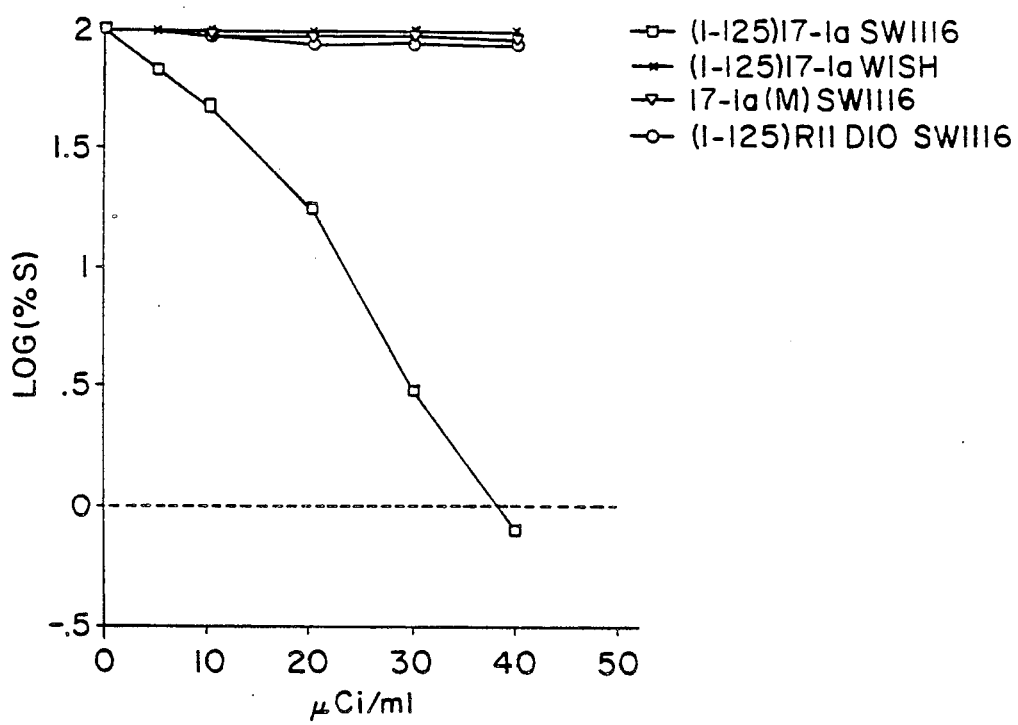
FIG. 7 is a graph showing cell survival curves for SW1116 and WISH cells following exposure to $^{125}$I radiolabeled murine 17-1A and chimeric 17-1A antibodies.
Figure 8:
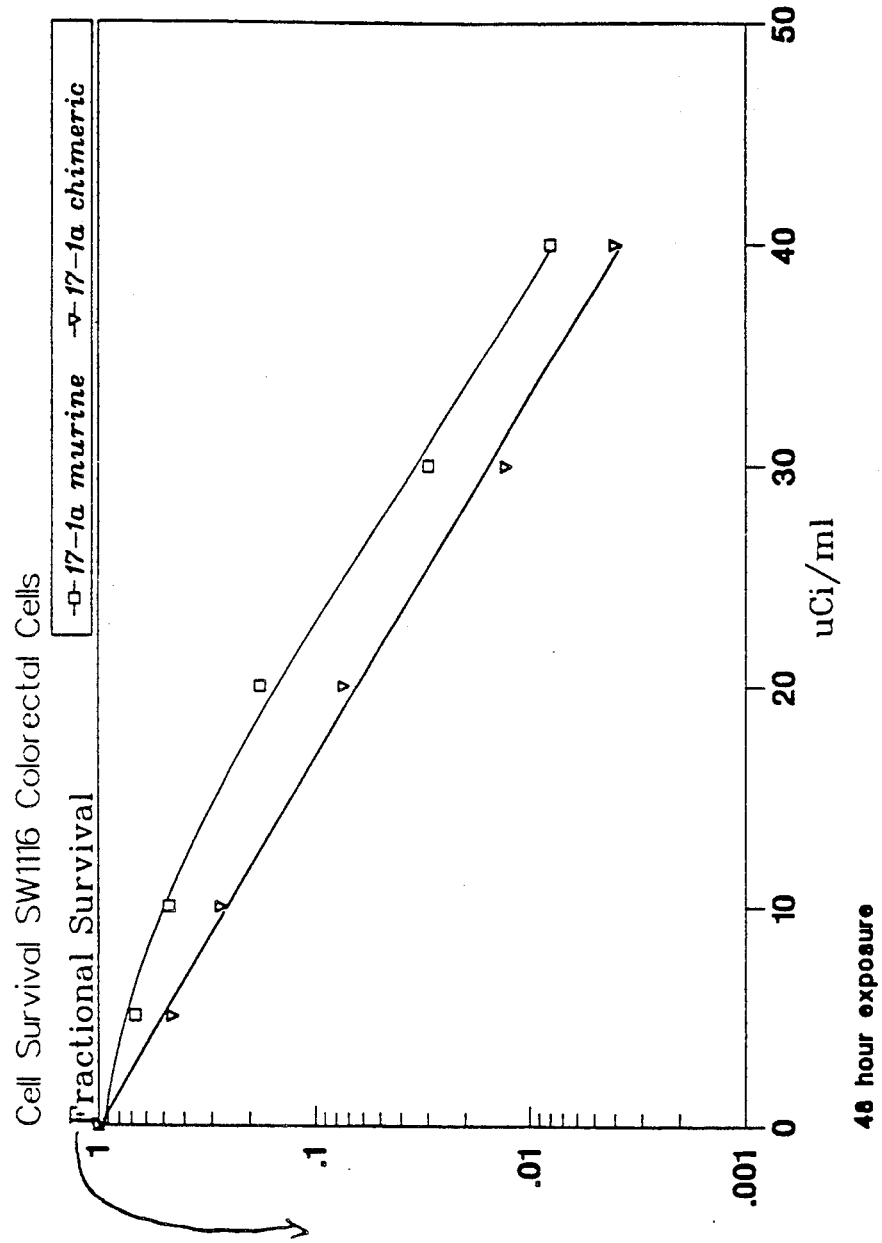
FIG. 8 is a graph showing cell survival curves for SW1116 cells exposed to chimeric 17-1a and murine 17-1a antibodies labeled with $^{125}$I for 48 hours.

The cell survival curve for $^{125}$I labeled MAb 17-1A indicates a 3 log reduction in colony counts (FIG. 7) as a function of increasing radioactive concentration (2.5 to 40 uCi/ml). The $^{125}$I labeled MAb 17-1A demonstrated non cytotoxicity on the WISH cell line and exposure of SW1116 cells to increasing nonradioactive MAb 17-1A concentration (1.4–5.6×10$-9$ M) had no effect on colony survival. Also, the effect of radiolabeled $^{125}$I-R11D10 (nonimmunoreactive antibody) had no effect on cell survival. FIG. 8 is a graph showing the effect of $^{125}$I-labeled murine and chimeric 17-1A antibodies on the survival of SW1116 colorectal cancer cells. The graph shows that after 48 hours exposure, only a fraction (<0.01%) of the cells survive. These results suggest that the $^{125}$I is responsible for causing decreased survival of cells containing antigen specific to the radiolabeled MAb 17-1A since cell which do not contain antigen are not affected by the $^{125}$I.

Chimeric 17-1A (c17-1A) IgG was radiolabeled with $^{125}$I and compared to $^{125}$I 17-1A IgG (murine) in cell survival studies. Both monoclonal antibodies (c17-1A and murine 17-1A) were labeled to the same specific activity (10 mCi/mg) with $^{125}$I. The experimental methods described above were used to obtain the survival curve. It was anticipated that the cell survival curve for the $^{125}$I c17-1A would be similar to the murine 17-1A since they have similar binding and immunoreactivity properties against SW1116 cells.

When the survival curves were obtained for the $^{125}$I c17-1A, it was discovered that the curve was a straight line as opposed to having a slight shoulder on the low dose portion of the curve obtained for the murine $^{125}$I 17-1A. This finding suggested something different about the way the c17-1A may behave after internalization into the cell. It is known that "shoulders" on typical survival curves indicate secondary mechanisms of radiation damage and that repair mechanisms do occur at low ionizing dose rates. Such curves are generated for standard irradiation of cells with sparsely ionizing radiation such as x-rays. However, the curve generated for cells exposed to the $^{125}$I c17-1A is a straight line as would be normally expected for densely ionizing radiation or radiation damage due to the direct effect. $^{125}$I has been found to behave like densely ionization radiation (high LET effect) when it was concentrated within the nuclear DNA. Our initial results with the murine 17-1A suggested that damage to the cell, while specific for only tumor cells, may be caused by more irradiation of nucleus from the cytoplasm than by direct nuclear irradation due to nonspecific binding of the radiolabeled 17-1A to the nucleus. Preferrably, it would have been nice if more radiolabeled murine 17-1A bound directly to the nucleus to produce greater damage to the cell.

On the other hand, the straight line survival curve obtained for the radiolabeled c17-1A indicated a different degree of radiation damage due to more nuclear incorporation of the $^{125}$I. This finding was unexpected and may be due to the unique differences between the human heavy and light chain constant regions compared to the mouse which enabled the c17-1A after internalization to bind more directly to the nucleus. It is possible that the unique amino acid sequence within the heavy and light chain constant regions and Fc regions may confer a greater degree of nuclear localization once the antibody is inside the cell. This phenomenon has been observed with so called nuclear transport location signals which allow large macromolecular protein to become transported through the nuclear membrane directly into the nucleus. Reference exist to support this phenomenon. It is quite possible the such a sequence may already be encoded directly into the chimeric 17-1A amino acid sequence which is not found in the murine version of the 17-1A. Furthermore, if this is true than it may be possible to encode this sequence into other monoclonal antibody producing clones to generate better monoclonal antibodies which are significantly more radiotoxic with $^{125}$I.

DISCUSSION

It has been found that exposure of 17-1A-positive tumor cells with an immunoconjugate comprising a monoclonal antibody specific for CA17-1A and $^{125}$I can result in lethal effects. It is believed that the first requirement for such lethal effects to occur is that the antigen-antibody complex undergo internalization into the cell. The second requirement is believed to be $^{125}$I binding to the nucleus of the tumor cell whereby the maximum effect due to the subcellular range of Auger electrons is achieved. The radiation damage to the cell is ultimately due to chromosomal damage in which much of the existing data strongly indicates that $^{125}$I when incorporated into DNA can result in irreparable damage and efficient cell killing.

The foregoing studies indicate that radiolabeled MAb 17-1A meets the first requirement by becoming significantly internalized after binding to specific cell membrane associated antigen. The internalization of $^{125}$I labeled MAb 17-1A results in 29.7% of total cell associated radioactivity being incorporated into the cell at 4 hours which increased to 49% at 48 hours. During these time periods, no dehalogenation or release of iodine back into the extracullar medium has been observed, using standard chromatography methods to detect any free iodide ion in the extracellular fluids and supernatants (after centrifugation and washing) during the incubation periods. The 17-1A MAb is particularly resistant to degradation in the cell, and does not release iodine break-down products. The chimeric 17-1A Mab (c17-1A) is even more resistant to degradation than the murine Mab, both in vitro and in vivo.

The maximum binding of $^{125}$I labeled MAb 17-1A in SW1116 cells appears to plateau at around 10 $\mu$Ci/ml concentration. The amount of radioactivity calculated becomes constant at about 0.67 pCi/cell. Assuming that 29 to 49% of total radioactivity bound to the cell is internalized, then 0.19 to 0.33 pCi is associated with the intracellular volume of the cell. This value is approximately 5 to 10 times higher than the uptake per cell of $^{125}$I iododeoxyuridine (0.035 pCi/cell) required to achieve a 37% survival in V79 Chinese hamster cells. However, in our experiments the fraction of radioactivity internalized that becomes associated with the nucleus has not been determined and could be significantly less, but still be more than adequate to produce lethal consequences in the affected cells if associated directly with the nucleus and DNA.

The nuclear damage associated with $^{125}$I incorporated into the nucleus results in characteristic radiation damage of the chromosomes. This damage manifests itself as the number of chromosome breaks (CB) as well as micronuclei (MN) and is proportional to the radioactive concentration in the nucleus. The foregoing studies show a similar dose dependent response related to increased chromosomal damage due to incorporation of radiolabeled MAb 17-1A which is specific to only tumor cells containing the requisite antigen. Control agents such as Na$^{125}$I, $^{125}$I labeled R11D10 antibody, and $^{125}$I labeled 116-NS-19-9 antibody did not result in an appreciable increase in chromosonal damage at similar radioactive concentrations in the SW1116 cell line. However, radioactive 116-NS-19-9 did show a slight increase in chromosomal abberations that does not appear to be dose dependent. Since the 116-NS-19-9 monoclonal antibody does bind to another tumor associated antigen on the SW1116 cell line which is shed into the extracellular medium, it is possible that the antigen-antibody complex may be taken up into these cells during the incubation period due to phagocytotic activity rather than direct internalization. Our studies further indicated that radioactive 116-NS-19-9 does not appear to be internalized as shown in FIG. 3. Furthermore, it appears that unless the specific antigen is present on the tumor cell, cells which do not contain the antigen (WISH cell line) are not affected by the radiolabeled tumor specific antibody and no increase in chromosomal abberations are observed above normal background levels.

Regardless on the cell system used, chromosomal damage induced by radiation is highly correlated to increased lethality resulting in a diminished cell survival. The cytoxcity of $^{125}$I labeled MAb 17-1A was determined using cell survival data. Nonimmunoreactive radiolabeled antibody and cells containing no antigen are not affected by the radioiodinated MAb 17-1A. The nonantigenic WISH cell line used for these studies have similar radiation sensitivities to the SW1116 cell line based upon cell survival studies using photon irradiation. However, because $^{125}$I Auger electron lethality is by the direct effect as with high LET radiation, varying degrees of radiation sensitivities by x-ray photons would probably have little or no effect on the direct action of Auger electrons in the DNA. The length of time for the incubations of cells with the radioactive test agents were 48 hours. When incubations were carried out for only 4 hours, no affect on cell survival was observed with the SW1116 cell line and $^{125}$I labeled MAb 17-1A. This factor may be attributable to the amount of internalization of the radioactive antibody which increased with time. The affect of an internalized tumor specific monoclonal antibody labeled with $^{125}$I on cell survival appears to be dose dependent on the amount of $^{125}$I that is retained in the cell.

In comparison to the internalization of $^{125}$IUdR in V79 cells, nuclear uptake is solely dependent upon mitotic activity while with a radiolabled monoclonal antibody, other factors important for internalizing and nuclear binding may be involved and not necessarily be related only to cellular division. The survival curve obtained for $^{125}$I labeled MAb 17-1A in SW1116 cells appears to have a slight shoulder which suggests that the $^{125}$I lethality may not be similar to high LET radiation as has been suggested for $^{125}$IUdR when incorporated into DNA. However, the radiation induced damage of $^{125}$I Auger electrons may be modified in the presence of oxygen suggesting that secondary mechanisms which generate reactive free radicals may be also responsible for cellular damage. In addition, the highly lethal damage of $^{125}$I to the DNA may be resultant of the large positively charged $^{125}$Te daughter atom (+8) which may cause direct chemical changes within biologically sensitive molecules.

These studies reflect the critical importance of specific cellular binding, internalization, and nuclear interaction, for promoting individual tumor cell cytotoxicity using certain $^{125}$I radiolabeled monoclonal antibodies such as MAb 17-1A. The primary mechanism of cell killing is understood in general terms of highly localized energy deposition within the DNA. Theoretical and experimental arguments for the apparent high LET toxicity of $^{125}$I support the notion of electron energy deposition (315 ev) of Auger electrons within a sphere of 10-Angstrom radius around the decay site within the DNA. The expected energy density has to be postulated to be equivalent to $1.3 \times 10^9$ rads per decay. Therefore, it has been predicted that a short segment of DNA corresponding to about three base pairs long on either side of the decay event should be severely affected resulting in multiple strand breaks and base damage.

The ability of tumor specific $^{125}$I labeled monoclonal antibodies to cause specific tumor cell destruction in vivo offers a distinct advantage for radioimmunotherapy. Radioiodination handling procedures and techniques are relatively simple, safe (low radiation exposure) and economic to perform yielding high specific activity product. Radioiodine-125 exposure to nontumor cells does not appear to cause any harm, and certainly whole body exposure from the weak iodine x-rays probably will not be of major concern when treating patients with large dosages of radioactive iodine. Other radionuclides such as $^{131}$I, $^{90}$Y, and alpha emitters have substantially higher particulate radiations and have the capability to destroy significantly more than just the tumor cells, thereby causing potentially more radiotoxicity. It is believed that the ability of circulating $^{125}$I labeled monoclonal antibodies to destroy individual tumor cells without harming nontumor cells will make such therapy ideal candidates as adjuvants to standard cancer treatments should there be a likelihood for recurrence or metastatic disease.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for delivering a cytotoxic radionuclide to the nuclei of tumor cells in vivo comprising contacting the tumor cells with an immunoconjugate comprising monoclonal antibody 17-1A, or a fragment thereof, labeled with $^{125}$I, wherein the monoclonal antibody is capable of localizing the radionuclide at the tumor cell nucleus.

2. A method for delivering a cytotoxic radionuclide to the nuclei of tumor cells in vivo comprising contacting the tumor cells with an immunoconjugate comprising monoclonal antibody c17-1A, or a fragment thereof, labeled with $^{125}$I, wherein the monoclonal antibody is capable of localizing the radionuclide at the tumor cell nucleus.

3. A method for treating a patient having a 17-1A positive malignancy comprising administering to the patient a therapeutically effective amount of a radiotherapeutic immunoconjugate consisting essentially of a monoclonal antibody, or fragment thereof, specific for CA 17-1A and $^{125}$I, wherein the antibody or fragment is capable of localizing the $^{125}$I radionuclide in the nuclei of the malignant cells.

4. A method according to claim 3, wherein the radiotherapeutic immunoconjugate is administered in an amount of from about 20 to 200 milliCuries of radioactivity representing mass quantities of antibody of about 2 to 20 mg.

* * * * *